US008841320B2

(12) United States Patent
Bornhop et al.

(10) Patent No.: US 8,841,320 B2
(45) Date of Patent: *Sep. 23, 2014

(54) TARGETED, NIR IMAGING AGENTS FOR THERAPY EFFICACY MONITORING, DEEP TISSUE DISEASE DEMARCATION AND DEEP TISSUE IMAGING

(71) Applicant: Vanderbilt University, Nashville, TN (US)

(72) Inventors: Darryl J. Bornhop, Nashville, TN (US); H. Charles Manning, Nashville, TN (US); Mingfeng Bai, Nashville, TN (US); Shelby Wyatt Sinha, Nashville, TN (US)

(73) Assignee: Vanderbilt University

( * ) Notice: Subject to any disclaimer, the term of this patent is extended or adjusted under 35 U.S.C. 154(b) by 0 days.

This patent is subject to a terminal disclaimer.

(21) Appl. No.: 13/765,453

(22) Filed: Feb. 12, 2013

(65) Prior Publication Data

US 2013/0177502 A1 Jul. 11, 2013

Related U.S. Application Data

(62) Division of application No. 12/835,448, filed on Jul. 13, 2010, now Pat. No. 8,372,868, which is a division of application No. 11/149,602, filed on Jun. 10, 2005, now Pat. No. 7,754,884.

(60) Provisional application No. 60/641,091, filed on Jan. 3, 2005.

(51) Int. Cl.
*C07D 209/56* (2006.01)
*A61K 31/47* (2006.01)

(52) U.S. Cl.
USPC .......................................... 514/307; 546/144

(58) Field of Classification Search
None
See application file for complete search history.

(56) References Cited

U.S. PATENT DOCUMENTS

| | | | |
|---|---|---|---|
| 5,091,381 | A | 2/1992 | Kim et al. |
| 5,268,486 | A | 12/1993 | Waggoner et al. |
| 5,928,627 | A | 7/1999 | Kiefer et al. |
| 6,027,709 | A | 2/2000 | Little et al. |
| 6,379,649 | B1 | 4/2002 | Katsifis et al. |
| 7,338,651 | B2 | 3/2008 | Bornhop et al. |
| 7,549,424 | B2 | 6/2009 | Desai |
| 7,754,884 | B2 | 7/2010 | Bornhop et al. |
| 8,188,116 | B2 * | 5/2012 | Bornhop et al. ............. 514/307 |
| 2003/0152518 | A1 | 8/2003 | Tidmarsh et al. |
| 2004/0266746 | A1 | 12/2004 | Rosen et al. |
| 2008/0031823 | A1 | 2/2008 | Bornhop et al. |
| 2008/0241074 | A1 | 10/2008 | Bornhop et al. |
| 2008/0241873 | A1 | 10/2008 | Bornhop et al. |
| 2009/0105128 | A1 | 4/2009 | Bornhop et al. |
| 2010/0278739 | A1 | 11/2010 | Bornhop et al. |
| 2010/0324130 | A1 | 12/2010 | Bornhop et al. |

FOREIGN PATENT DOCUMENTS

| | | |
|---|---|---|
| AU | 2002323528 | 3/2008 |
| CA | 2459724 | 2/2011 |
| EP | 1429783 | 6/2004 |
| EP | 1841466 | 10/2007 |
| WO | WO9849900 | 11/1998 |
| WO | WO03020701 | 3/2003 |
| WO | WO2006074129 | 7/2006 |

OTHER PUBLICATIONS

Ahmad, et al.; Major liver resection in the elderly; ASGBI: Br. J. Surg. vol. 89, Suppl. 1; Jun. 2002; pp. 62-64.

Alho, et al.; Expression of Mitochondrial Benzodiazepine Receptor and Its Putative Endogenous Ligand in Cultured Primary Astrocytes and C-6 Cells—Relation to Cell-Growth. Cell Growth & Differentiation 1994;5:1005-1014.

Benavides, et al. Imaging of Human-Brain Lesions with an Omega-3 Site Radioligand. Annals of Neurology 1988;24:708-712.

Black, et al.; Imaging of Brain-Tumors Using Peripheral Benzodiazepine Receptor Ligands. Journal of Neurosurgery 1989;71:113-118.

Broaddus, et al.; Department of Neurosurgery UoVHSCC. Peripheral-type benzodiazepine receptors in human glioblastomas: pharmacologic characterization and photoaffinity labeling of ligand recognition site. Brain research. 1990;518(1-2):199-208.

Bromiley, et al. Attenuation correction in PET using consistency conditions and a three-dimensional template. Ieee Transactions on Nuclear Science 2001;48:1371-1377.

Casellas, et al.; Peripheral benzodiazepine receptors and mitochondrial function. Neurochemistry International 2002;40:475-486.

Cornu, et al.; Increase in Omega-3 (Peripheral-Type Benzodiazepine) Binding-Site Densities in Different Types of Human Brain-Tumors—a Quantitative Autoradiography Study. Acta Neurochirurgica 1992;119:146-152.

Czernin, et al.; Annu Rev Med 2002, 53, 89-112.

Dehdashti, et al.; Positron emission tomographic assessment of "metabolic flare" to predict response of metastatic breast cancer to antiestrogen therapy. European Journal of Nuclear Medicine 1999;26:51-56.

Diorio, et al.; Peripheral Benzodiazepine Binding-Sites in Alzheimers-Disease Frontal and Temporal Cortex. Neurobiology of Aging 1991;12:255-258.

Ernst, et al., Cytometry 10:3-10 (1989).

(Continued)

*Primary Examiner* — Zinna Northington Davis
(74) *Attorney, Agent, or Firm* — Stites & Harbison PLLC; Richard S. Myers, Jr.

(57) ABSTRACT

Compounds and methods related to NIR molecular imaging, in-vitro and in-vivo functional imaging, therapy/efficacy monitoring, and cancer and metastatic activity imaging. Compounds and methods demonstrated pertain to the field of peripheral benzodiazepine receptor imaging, metabolic imaging, cellular respiration imaging, cellular proliferation imaging as targeted agents that incorporate signaling agents.

19 Claims, 6 Drawing Sheets

(56) References Cited

OTHER PUBLICATIONS

Faulkner, et al.; Lanthanide-sensitized lanthanide luminescence: Terbium-sensitized ytterbium luminescence in a trinuclear complex. Journal of the American Chemical Society 2003;125:10526-10527.
Fennell, et al.; Bcl-2 resistant mitochondrial toxicity mediated by the isoquinoline carboxamide PK11195 involves de novo generation of reactive oxygen species. British Journal of Cancer 2001;84:1397-1404.
Francis et al. Eur J Nucl Med Mol Imaging 2003, 30, 988-994.
Gaietta, et al. Multicolor and electron microscopic imaging of connexin trafficking. Science 2002;296:503-507.
Gonzalez-Polo, et al.; PK11195 potently sensitizes to apoptosis induction independently from the peripheral benzodiazepine receptor; Oncogene 2005; 24; 7503-7513.
Griffin, et al.; Simple, high yielding synthesis of trifunctional fluorescent lanthanide chelates. Tetrahedron Letters 2001;42:3823-3825.
Hardwick, et al.; Peripheral-type benzodiazepine receptor (PBR) in human breast cancer: Correlation of breast cancer cell aggressive phenotype with PBR expression, nuclear localization, and PBR-mediated cell proliferation and nuclear transport of cholesterol. Cancer Research 1999;59:831-842.
Hawrysz, et al.; Developments toward diagnostic breast cancer imaging using near-infrared optical measurements and fluorescent contrast agents. Neoplasia 2000;2:388-417.
Jakubikova, et al.; PK11195, an isoquinoline carboxamide ligand of the mitochondrial benzodiazepine receptor, increased drug uptake and facilitated drug-induced apoptosis in human multidrug-resistant leukemia cells in vitro. Neoplasma 2002;49:231-236.
Kozikowski; et al.; Papadopoulos V. Synthesis and Biology of a 7-Nitro-2,1,3-benzoxadiazol-4-yl Derivative of 2-Phenylindole-3-acetamide: A Fluorescent Probe for the Peripheral-Type Benzodiazepine Receptor. Journal of Medicinal Chemistry 1997;40:2435-2439.
Lemieux, et al.; Exploiting differences in sialoside expression for selective targeting of MRI contrast reagents. Journal of the American Chemical Society 1999;121:4278-4279.
Licha, et al.; Hydrophilic cyanine dyes as contrast agents for near-infrared tumor imaging: Synthesis, photophysical properties and spectroscopic in vivo characterization. Photochemistry and Photobiology 2000;72:392-398.
Louie, et al. In vivo visualization of gene expression using magnetic resonance imaging. Nature Biotechnology 2000;18:321-325.
Maaser, et al. Specific ligands of the peripheral benzodiazepine receptor induce apoptosis and cell cycle arrest in human colorectal cancer cells. British journal of cancer. 2001;85(11):1771-80.
Manning, et al. Facile, efficient conjugation of a trifunctional lanthanide chelate to a peripheral benzodiazepine receptor ligand. Organic Letters 2002;4:1075-1078.
Manning, et al. Targeted Molecular Imaging Agent for Cellular-Scale Bi-modal Imaging. Bioconjugate Chemistry 2004, 15, 1488-1495.
Medina, et al.;. Biol Res 2002, 35, 9-26.
Messmer, et al. Increased peripheral benzodiazepine binding sites in the brain of patients with Huntington's disease. Neuroscience Letters 1998;241:53-56.
Narayanan, et al.; J. Org. Chem. 60:2391-5 (1995).
Ntziachristos, et al.; Probing physiology and molecular function using optical imaging: applications to breast cancer. Breast Cancer Research 2001;3:41-46.
Okaro, et al.; PK11195 a mitochondrial benzodiazepine receptor antagonist, reduces apoptosis threshold in Bcl-Xl and Mcl-1 expressing human cholangiocarcinoma cells. Gut 2002;51:556-561.
Oyama, et al. C-11-acetate PET imaging of prostate cancer: Detection of recurrent disease at PSA relapse. Journal of Nuclear Medicine 2003;44:549-555.
Oyama, et al. MicroPET assessment of androgenic control of glucose and acetate uptake in the rat prostate and a prostate cancer tumor model. Nuclear Medicine and Biology 2002;29:783-790.
Papadopoulos V. Peripheral-Type Benzodiazepine Diazepam Binding Inhibitor Receptor—Biological Role in Steroidogenic Cell-Function. Endocrine Reviews 1993;14:222-240.
Shavaleev, et al. Bell ZR, Faulkner S, Ward MD. Visible-light sensitisation of near-infrared luminescence from Yb(III), Nd(III) and Er(III) complexes of 3,6-bis(2-pyridyl)tetrazine. Dalton Transactions 2003:808-814.
Starosta-Rubinstein, et al.; Imaging of a glioma using peripheral benzodiazepine receptor ligands. proceedings of the national academy of sciences of the United States of America 1987;84:891-5.
Sutter, et al.; Specific ligands of the peripheral benzodiazepine receptor induce apoptosis and cell cycle arrest in human esophageal cancer cells. International journal of cancer. Journal international du cancer. 2002;102(4):318-27.
Vejdelek, et al.; Synthesis of 7-Chloro-5-(4-Chlorophenyl)-1-Methyl-1,3-Dihydro-1,4-Benzodiazepin-2-One. Collection of Czechoslovak Chemical Communications 1985;50:1064-1069.
Vowinckel, et al. PK11195 binding to the peripheral benzodiazepine receptor as a marker of microglia activation in multiple sclerosis and experimental autoimmune encephalomyelitis. Journal of Neuroscience Research 1997;50:345-353.
Walker, et al.,; PK11195, a peripheral benzodiazepine receptor (pBR) ligand, broadly blocks drug efflux to chemosensitize leukemia and myeloma cells by a pBR-independent, direct transporter-modulating mechanism; Blood 2005; 106:10; 3584-3593.

* cited by examiner

Figure 3.8 (A) white light picture of dosed cells; (B) fluorescence picture of dosed cells; (C) white light picture of un-dosed cells; (D) fluorescence picture of un-dosed cells

TARGETED, NIR IMAGING AGENTS FOR THERAPY EFFICACY MONITORING, DEEP TISSUE DISEASE DEMARCATION AND DEEP TISSUE IMAGING

PRIORITY INFORMATION

This application is a divisional of Ser. No. 12/835,448 filed Jul. 13, 2010, now U.S. Pat. No. 8,372,868, which is a divisional of Ser. No. 11/149,602 filed Jun. 10, 2005, now U.S. Pat. No. 7,754,884 which claims priority to U.S. Patent Application No. 60/641,091, the contents of which are incorporated herein by reference.

FIELD OF THE INVENTION

This invention relates generally to the field of molecular imaging, and more specifically to the field of functional imaging, including glucose transporters, thymidine kinase activity, and peripheral benzodiazepine receptors as targeted agents that incorporate near-infrared fluorophores as signaling agents.

BACKGROUND OF THE INVENTION

Current state-of-the-art detection and surgical resection tools used in cancer treatment are insufficient. Early stage disease can be missed, resection can be incomplete and these two factors alone are major contributors to morbidity and mortality. Outcomes are intrinsically linked to disease detection and treatment efficacy. Therefore, improvement in the detection of early cellular changes, as well as enhanced visualization of diseased tissue, is of paramount importance.

Optical methods continue to provide a powerful means for studying cell and tissue function. Recent discoveries in Molecular Imaging (MI) are certain to play a vital role in the early detection, diagnosis, and treatment of disease. MI will also aid in the study of biological and biochemical mechanisms, immunology, and neuroscience. MI agents commonly consist of a signaling moiety (fluorophore, radioisotope or $Gd^{3+}$ ion) and a targeting functionality such as an antibody or peptide, sugar or a peripheral benzodiazepine receptor (PBR) ligand. NIR molecular imaging agents are particularly attractive due to the inherently low water and tissue absorption in the NIR spectral region. Additionally, the low scattering cross-section and lack of autofluorescence background in the near infrared (NIR) region facilitate deep penetration and high-resolution images from small interrogated volumes.

While glandular and secretory tissues are normally rich in PBR, other quiescent tissue ordinarily express PBR at relatively low levels. Primarily spanning the bi-layered mitochondrial membrane, the PBR is expressed almost ubiquitously and thought to be associated with many biological functions including the regulation of cellular proliferation, immunomodulation, porphyrin transport, heme biosynthesis, anion transport, regulation of steroidogenesis and apoptosis. Given the importance of PBR toward regulating mitochondrial function, it is not surprising that PBR density changes have been observed in acute and chronic neurodegenerative states in humans, as well as numerous forms of cancer. For example, temporal cortex obtained from Alzheimer's patients showed an increase in PBR, and correlations with Huntington's disease, multiple sclerosis and gliosis have been demonstrated. Breast cancer generally demonstrates increased PBR expression and represents another potentially attractive target, especially in the NIR. The development of high affinity ligands for PBR (such as, for example, PK-11195, Ro5-4864, DAA1106, and DAA1107) has made non-invasive imaging modalities more suitable.

Other functional imaging targets include the glucose transporter and thymidine kinase 1. By targeting the glucose transporter, [$^{18}$F]-fluoro-deoxyglucose (FDG) has been successfully employed as a positron emission tomography (PET) agent to determine the metabolic statues (cellular respiration) of suspect tissues. Modest functionalization of glucose at the C-2 position does not hinder sugar uptake but does prevent cellular metabolism, therefore glucose agents can accumulate intracellularly. Since tumor cells metabolize glucose a higher rate than normal cells, the accumulation of glucose mimics (i.e. FDG and similar agents) can facilitate discrimination of tissues based on their metabolic status. While FDG imaging certainly has demonstrated utility to the clinical oncologist, the requirement of a cyclotron and a PET scanner somewhat limit its use.

Recently, in effort to improve the specificity of functional imaging agents like FDG, new probes for cellular proliferation imaging have been developed. Targeting the enzyme thymidine kinase 1 (TK1), an enzyme responsible for DNA replication, [$^{18}$F]3'-deoxy-3' fluorothymidine (FLT) has been shown to be an attractive complement to FDG imaging. Similar to FDG, FLT is not fully metabolized by cells and accumulates in target tissues, making it a promising imaging agent for rapidly proliferating tissues. When used in combination with FDG, clinical imaging of diseased tissue has the ability to be highly sensitive and specific.

It has been shown that NIR emitting Ln-Chelates can be prepared opening the avenue to complexes with spectral properties more compatible with biological imaging such as visible absorption, NIR emission and microsecond-long emission lifetimes. These complexes have high molar absorptivity and have luminescent lifetimes in the microsecond regime allowing temporal rejection of noise.

The present inventors have demonstrated the synthesis and utility of Eu-PK11195 and Gd-PK11195. Others have prepared PK11195 as a PET agent for use in humans. A NIR Pyropheophorbide agent has been reported for imaging glucose transporters, however this agent was not spectroscopically optimized for deep tissue in-vivo imaging (ex. 679 nm, em. 720 nm). At present, the authors are unaware of any NIR imaging agents based on thymidine imaging.

SUMMARY OF THE INVENTION

The peripheral benzodiazepine receptor (PBR) has been shown an attractive target for contrast-enhanced imaging of disease. See Publication No. 2003/0129579, incorporated herein by reference. Embodiments of the present invention include PBR targeted agents which incorporate near-infrared (NIR) fluorophores as signaling agents. Aspects of the present invention include a previously unknown class of NIR absorbing/emitting PBR targeted contrast agents which utilize a conjugable form of PK11195 as a targeting moiety.

Additionally, aspects of the present invention include the synthesis of NIR-metabolic and proliferation probes. The authors report a sacharide agent suitable for metabolic imaging in similar fashion to $^{18}$FDG and a NIR-thymidine probe suitable for imaging cellular proliferation (DNA synthesis). The NIR contrast agents disclosed herein are suitable for optical imaging using spectral and time-gated detection approaches to maximize the signal-to-background ratio. High molar extinction dyes that absorb and emit in the NIR, such as IRdye800CW™ (available from LiCOR) and CY7 (Amersham), as well as NIR Lanthanide chelates are demonstrated.

Since thymidine, PK11195 and other PBR ligands have been suggested as therapeutic agents, the molecules demonstrated here could also be useful therapeutics which also offers direct monitoring of dose delivery and therapeutic efficacy.

With absorption and emission closer to the tissue transparency window (780 nm, 830 nm respectively), the dyes reported here are much more suited for in-vivo imaging. Additionally, no one has demonstrated NIR PBR ligands for imaging PBR expression and/or therapy.

Thus, one aspect of the present invention is a method of imaging a molecular event in a sample, the method steps comprising administering to the sample a probe having an affinity for a target. The probe has at least one of a ligand/signaling agent combination, or conjugable form of a ligand/signaling agent combination. After the probe is administered, a signal from the probe may be detected. In embodiments of the present invention, the sample can be at least one of cells, tissue, cellular tissue, serum, cell extract, bodily fluids. The bodily fluids may be, for example, breast milk, sputum, vaginal fluids, urine.

Another aspect of the present invention is a method of measuring glucose uptake. This embodiment comprises the steps of administering to a sample a conjugate, the conjugate comprising a conjugable glucosamine compound and a signaling agent; and then detecting a signal from said conjugate. In embodiments of the present invention, the sample is at least one of cells, tissue, cellular tissue, serum, cell extract, bodily fluids.

Another aspect of the present invention is a method of quantifying the progression of a disease state progression that includes the steps of (a) administering to a first sample a conjugate that comprises a conjugable deoxythymidine compound and a signaling agent; (b) detecting a signal from the conjugate; (c) after a period of time from step (b), administering to a second sample a conjugate, (d) detecting a second signal; and (e) comparing the first signal with the second signal to determine the progress of a disease state. Again examples of the sample are at least one of cells, tissue, cellular tissue, serum, cell extract, bodily fluids.

Another aspect of the present invention is the above method, where the conjugate includes a peripheral benzodiazepine affinity ligand or conjugable form thereof and a signaling agent.

Another aspect of the present invention is the above method, where the conjugate includes a glucosamine compound and a signaling agent.

In the above embodiments and other embodiments of the present invention, the administration step is in vivo or in vitro.

DESCRIPTION OF THE INVENTION

Figure 1:
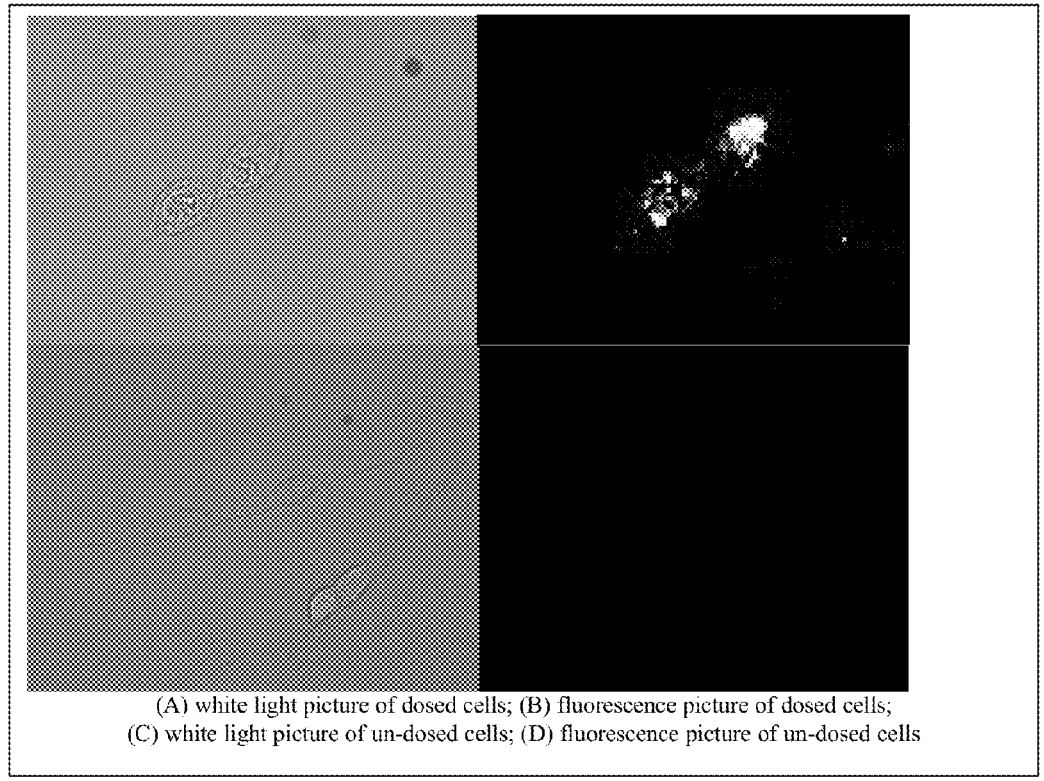
FIG. 1 is a color photograph that shows white light and fluorescence pictures of dosed cells and un-dosed cells in accordance with the present invention, and is further discussed in Example 6, below. Picture A is a white light picture of dosed cells, Picture B is a fluorescence picture of dosed cells, Picture C is a white light picture of un-dosed cells, and Picture D is a fluorescence picture of un-dosed cells.

Embodiments of the present invention include NIR agents for the PBR based on NIR dyes, including Lanthanide chelates. Additionally, complimentary imaging agents are disclosed using a novel NIR sacharide and NIR thymidine agent. Aspects of the present invention include both being used separately, as well as where the agents are used together as a cocktail whereby both PBR expression and metabolic and or cellular proliferation status could be simultaneously monitored in-vivo.

PBR ligands such as PK11195 have been suggested as therapeutic agents. Mitochondria localized anti-death proteins of the Bcl-2 family play a central role in inhibiting apoptosis and therefore present therapeutic targets. PBR shares a close physical association with the permeability transition pore complex (PTPC) and binding of PK11195 has been shown to cause Bcl-2 resistant generation of oxidative stress. The agents reported here are unique in that they facilitate in-vivo monitoring of therapeutic delivery and efficacy.

As stated above, aspects of the present invention include methods of imaging a molecular event. in a sample, the method steps comprising administering to the sample a probe having an affinity for a target. The probe has at least one of a ligand/signaling agent combination, or conjugable form of a ligand/signaling agent combination. One such ligand/signaling agent combination comprises PBR ligands, or conjugable forms thereof.

Examples of the PBR ligands of the present invention include conjugable forms, or conjugable analogs of the following compounds:

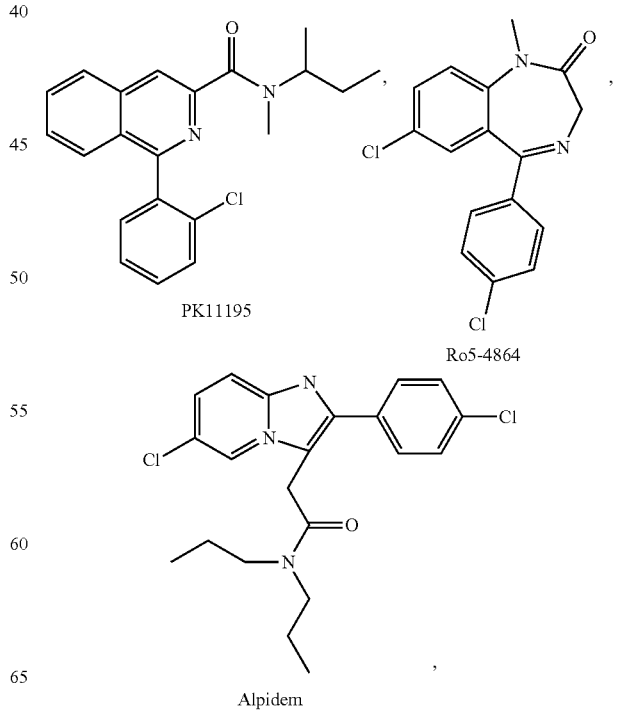

-continued

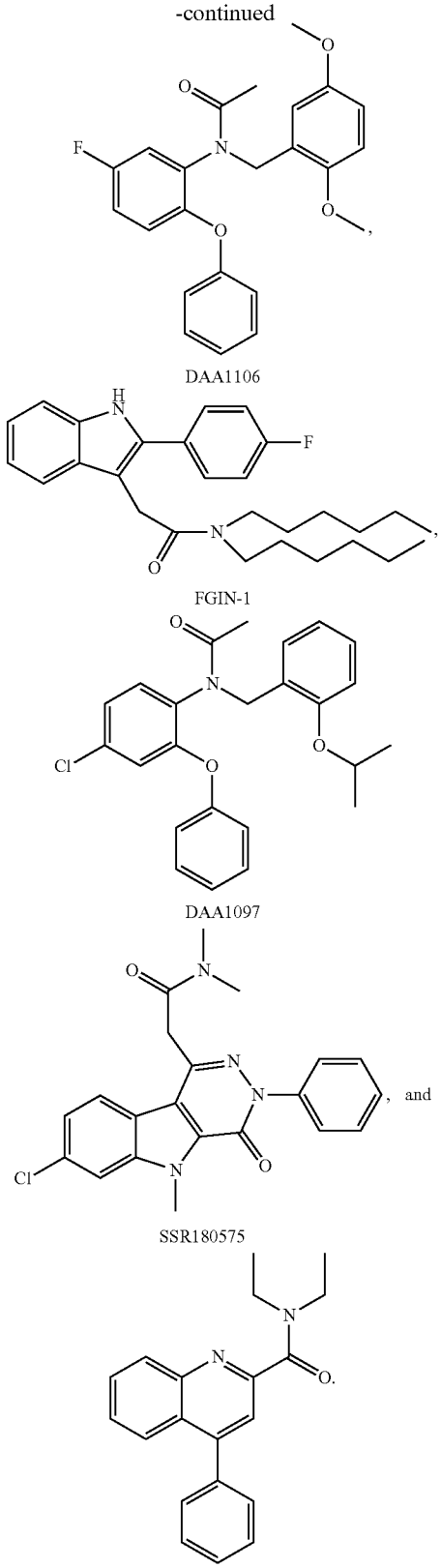

DAA1106

FGIN-1

DAA1097

SSR180575

, and

For the purposes of the present invention, the term analog encompases isomers, homologs, or other compounds sufficiently resembling the base compound in terms of structure and do not destroy activity. "Conjugable forms," "conjugable compounds," and similar terms describe a form of the compound that can readily form a covalent form a covalent bond with a signaling agent such as an IR dye.

For exemplary purposes, conjugable forms of PK11195, above, include at least the following compounds, and/or analogs or derivatives thereof:

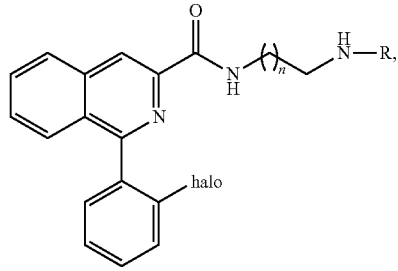

wherein R is H or alkyl, n is 0-10, and "halo" is fluorine, chlorine, bromine, iodine. In other embodiments of the present invention, halo is chlorine.

The term "halo" or "halogen," as used herein, includes radio isotopes of halogen compounds, such as $I^{121}$ and $F^{19}$.

Additionally, for exemplary purposes, conjugable forms of Ro5-4864 include the following and/or analogs or derivatives thereof:

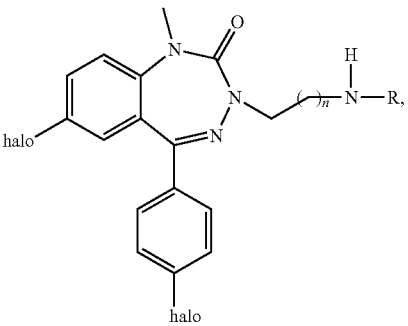

wherein the variables are defined above. In other embodiments of the present invention, halo is chlorine.

Additionally, for exemplary purposes, conjugable forms of DAA1106 include the following and/or analogs or derivatives thereof:

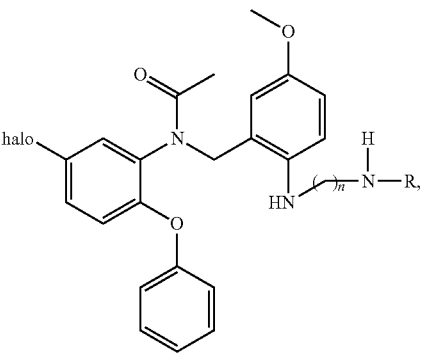

wherein the variables are defined above, and:

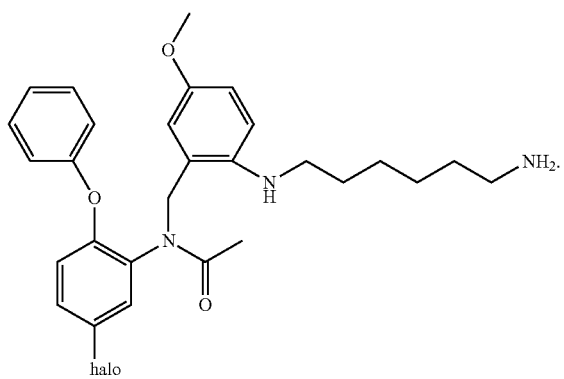

In other embodiments of the present invention, halo is chlorine or fluorine.

Additionally, for exemplary purposes, conjugable forms of SSR180575 include the following and/or analogs or derivatives thereof:

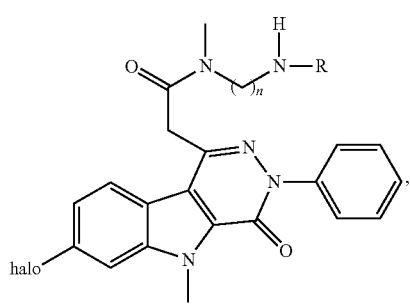

wherein the variables are defined above. In other embodiments of the present invention, halo is chlorine.

Non-limited examples of PBR ligands and signaling moieties include the following compounds:

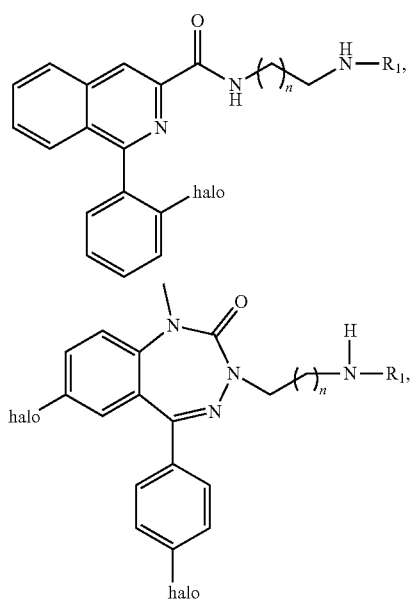

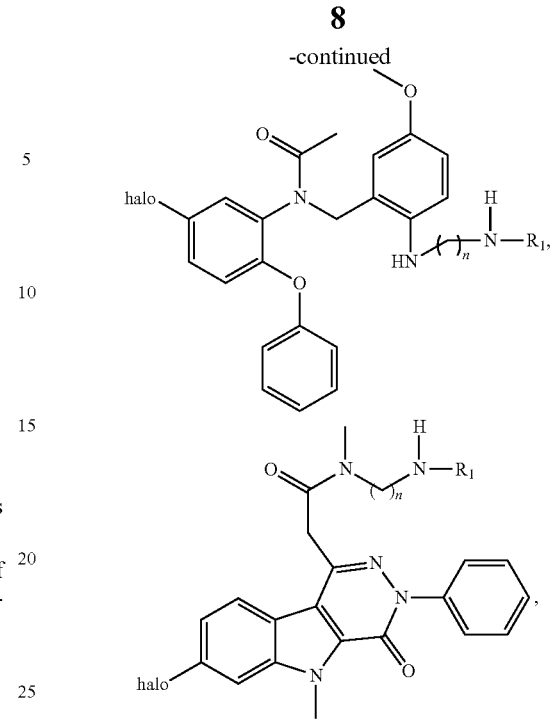

or an analog thereof, wherein $R_1$ is a signaling moiety; "halo" is fluorine, chlorine, bromine, iodine; and n is 0-10.

Preferably, in the above examples, the signaling moiety is a dye.

Additionally, other aspects of the present invention include NIR-sacharide agents suitable for metabolic imaging in similar fashion to $^{18}$FDG. Given the ubiquitous clinical use of $^{18}$FDG, 2-deoxyglucose derivatives have been extensively biologically characterized. See Czernin, J.; Phelps, M. E. *Annu Rev Med* 2002, 53, 89-112. These derivatives are useful metabolic imaging agents given the overexpression of glucose transporters and increased hexokinase activity in tumors. See Medina, R. A.; Owen, G. I. *Biol Res* 2002, 35, 9-26. 2-deoxyglucose imaging agents are incorporated into cells via the glucose transporter and are subsequently phosphorylated by hexokinase. In phosphorylating the probe, the neutral molecule becomes anionic and membrane impermeable. Functionalization at the 2-position prevents further metabolism, and thus the probe is trapped in the cells, with further uptake leading to significant accumulation. See Zhang, M.; Zhang, Z. H.; Blessington, D.; Li, H.; Busch, T. M.; Madrak, V.; Miles, J.; Chance, B.; Glickson, J. D.; Zheng, G. *Bioconjugate Chem* 2003, 14, 709-714.

Additionally, other aspects of the present invention include a NIR-thymidine probe for monitoring cellular proliferation, similar in fashion to [$^{18}$F]3'-deoxy-3' fluorothymidine (FLT). FLT has been used clinically and extensively compared to FDG. See Halter et al. *General Thoracic Surgery* 2004, 127, 1093-1099 and Francis et al. *Eur J Nucl Med Mol Imaging* 2003, 30, 988-994. In proliferating cells, FLT metabolism takes place within the anabolic arm of the DNA salvage pathway. TK1 controls entry into the salvage pathway and converts FLT to the mono-phosphate species. The agent is further phosphorylated, but can not be incorporated into DNA due to its lack of a hydroxyl group at 3'.

With respect to the signaling agents used in connection with the present invention, embodiments include near infrared signaling agents. Also includes are dyes, such as, for example, near-infrared fluorophores/fluorescent dyes.

Examples include cyanine dyes which have been used to label various biomolecules. See U.S. Pat. No. 5,268,486, which discloses fluorescent arylsulfonated cyanine dyes having large extinction coefficients and quantum yields for the purpose of detection and quantification of labeled components.

Additional examples include compounds of the following formulas:

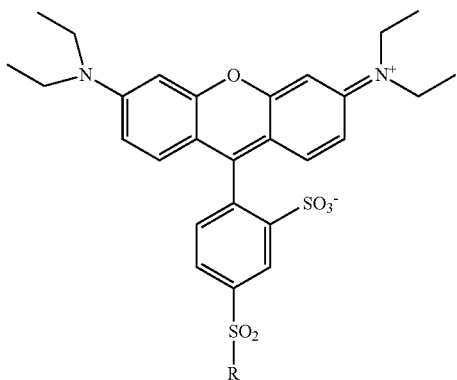

Lissamine-Rhodamine abs/em = 560 nm, 590 nm;

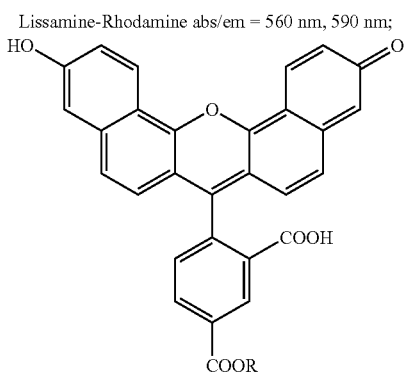

Carboxynaphthofluorescein abs/em = 580 nm, 690 nm

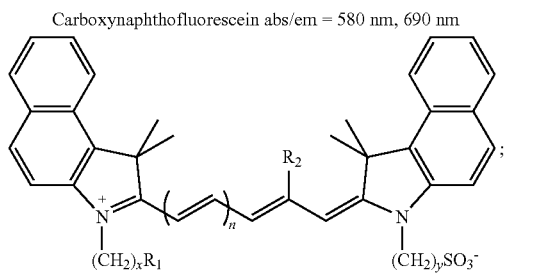

General Cyanine dye

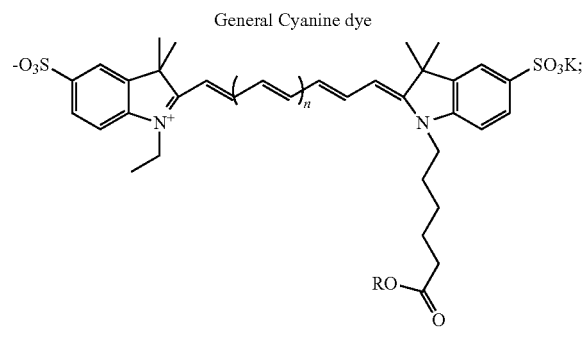

CY-Family of dyes and analogs thereof.

Additional examples include dyes available from Li-Cor, such as IR Dye 800CW™, available from Li-Cor.

Additional examples include dyes disclosed in U.S. Pat. No. 6,027,709.

US '709 discloses dyes which have the following general formula:

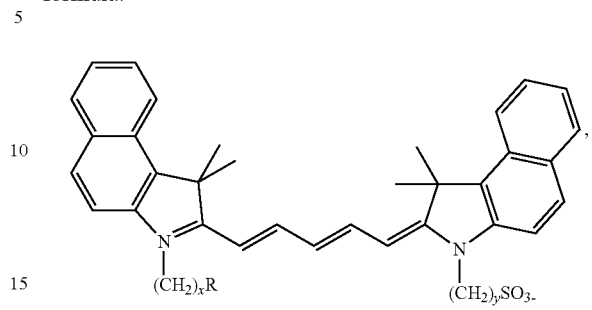

wherein R is —OH, —CO₂H, —NH₂, or —NCS and each of x and y, independently, is an integer selected from 1 to about 10. In preferred embodiments, each of x and y, independently, is an integer between about 2 and 6.

In one embodiment, the dye is N-(6-hydroxyhexyl)N'-(4-sulfonatobutyl)-3,3,3',3'-tetramethylbenz(e)indod icarbocyanine, which has the formula:

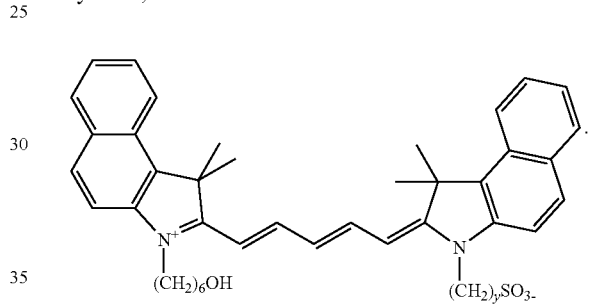

In a second embodiment, the dye is N-(5-carboxypentyl) N'-(4-sulfonatobutyl)3,3,3',3'-tetramethylbenz(e)indodicarbocyanine, which has the formula:

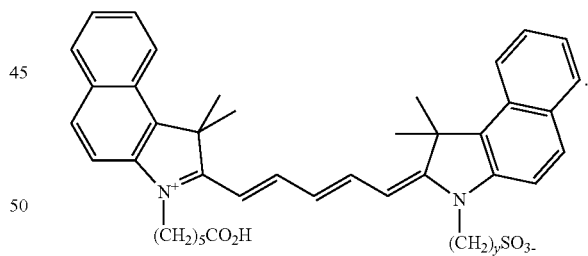

These two dyes are embodiments because they have commercially available precursors for the linking groups: 6-bromohexanol, 6-bromohexanoic acid and 1,4-butane sultone (all available from Aldrich Chemical Co., Milwaukee, Wis.). The linking groups provide adequate distance between the dye and the biomolecule for efficient attachment without imparting excessive hydrophobicity. The resulting labeled biomolecules retain their solubility in water and are well-accepted by enzymes.

These dyes, wherein R is —CO₂H or —OH can be synthesized, as set forth in detail in the US '709 patent, by reacting the appropriate N-(carboxyalkyl)- or N-(hydroxyalkyl)-1,1,2-trimethyl-1H-benz(e)indolinium halide, preferably bromide, with sulfonatobutyl-1,1,2-trimethyl-1H-benz(e)indole at a relative molar ratio of about 0.9:1 to about 1:0.9, preferably 1:1 in an organic solvent, such as pyridine, and heated to reflux, followed by the addition of 1,3,3-trimethoxypropene in a relative molar ratio of about 1:1 to about 3:1 to the reaction product and continued reflux. The mixture subsequently is cooled and poured into an organic solvent such as ether. The resulting solid or semi-solid can be purified by chromatography on a silica gel column using a series of methanol/chloroform solvents.

As an alternative, two-step, synthesis procedure, also detailed in U.S. '709, N-4-sulfonatobutyl-1,1,2-trimethyl-1H-benz(e)indole and malonaldehyde bis(phenylimine)-monohydrochloride in a 1:1 molar ratio can be dissolved in acetic anhydride and the mixture heated. The acetic anhydride is removed under high vacuum and the residue washed with an organic solvent such as ether. The residual solid obtained is dried and subsequently mixed with the appropriate N-(carboxyalkyl)- or N-(hydroxyalkyl)-1,1,2-trimethyl-1H-benz(e)indolinium halide in the presence of an organic solvent, such as pyridine. The reaction mixture is heated, then the solvent is removed under vacuum, leaving the crude desired dye compound. The procedure was adapted from the two step procedure set forth in Ernst, L. A., et al., Cytometry 10:3-10 (1989).

The dyes also can be prepared with an amine or isothiocyanate terminating group. For example, N-(omega.-aminoalkyl)-1,1,2-trimethyl-1H-benz(e)indolenium bromide hydrobromide (synthesized as in N. Narayanan and G. Patonay, J. Org. Chem. 60:2391-5 (1995)) can be reacted to form dyes of formula 1 wherein R is —NH$_2$. Salts of these amino dyes can be converted to the corresponding isothiocyanates by treatment at room temperature with thiophosgene in an organic solvent such as chloroform and aqueous sodium carbonate.

These dyes have a maximum light absorption which occurs near 680 nm. They thus can be excited efficiently by commercially available laser diodes that are compact, reliable and inexpensive and emit light at this wavelength. Suitable commercially available lasers include, for example, Toshiba TOLD9225, TOLD9140 and TOLD9150, Phillips CQL806D, Blue Sky Research PS 015-00 and NEC NDL 3230SU. This near infrared/far red wavelength also is advantageous in that the background fluorescence in this region normally is low in biological systems and high sensitivity can be achieved.

The hydroxyl, carboxyl and isothiocyanate groups of the dyes provide linking groups for attachment to a wide variety of biologically important molecules, including proteins, peptides, enzyme substrates, hormones, antibodies, antigens, haptens, avidin, streptavidin, carbohydrates, oligosaccharides, polysaccharides, nucleic acids, deoxy nucleic acids, fragments of DNA or RNA, cells and synthetic combinations of biological fragments such as peptide nucleic acids (PNAs).

In another embodiment of the present invention, the ligands of the present invention may be conjugated to a lissamine dye, such as lissamine rhodamine B sulfonyl chloride. For example, a conjugable form of DAA1106 may be conjugated with lissamine rhodamine B sulfonyl chloride to form a compound of the present invention.

Lissamine dyes are typically inexpensive dyes with attractive spectral properties. For example, examples have a molar extinction coefficient of 88,000 cm$^{-1}$M$^{-1}$ and good quantum efficient of about 95%. It absorbs at about 568 nm and emits at about 583 nm (in methanol) with a decent stokes shift and thus bright fluorescence.

Coupling procedures for the PBR ligands and Glucosamine proceed via standard methods and will be recognized by those skilled in the art. In general, the nucleophilic N terminus of the targeting moieties are reactive towards activated carbonyls, for example an NHS (N-hydroxysuccinimide ester), sulfonyl chlorides, or other electrophile bearing species. Solvent of choice for coupling reactions can be dye specific, but include dimethyl sulfoxide (DMSO), chloroform, and/or phosphate buffered saline (PBS buffer). The resulting conjugates, amides, sulfonamides, etc. resist hydrolysis under physiological conditions, and are thus useful for in-vivo and in-vitro application.

The following are examples of compounds of the present invention:

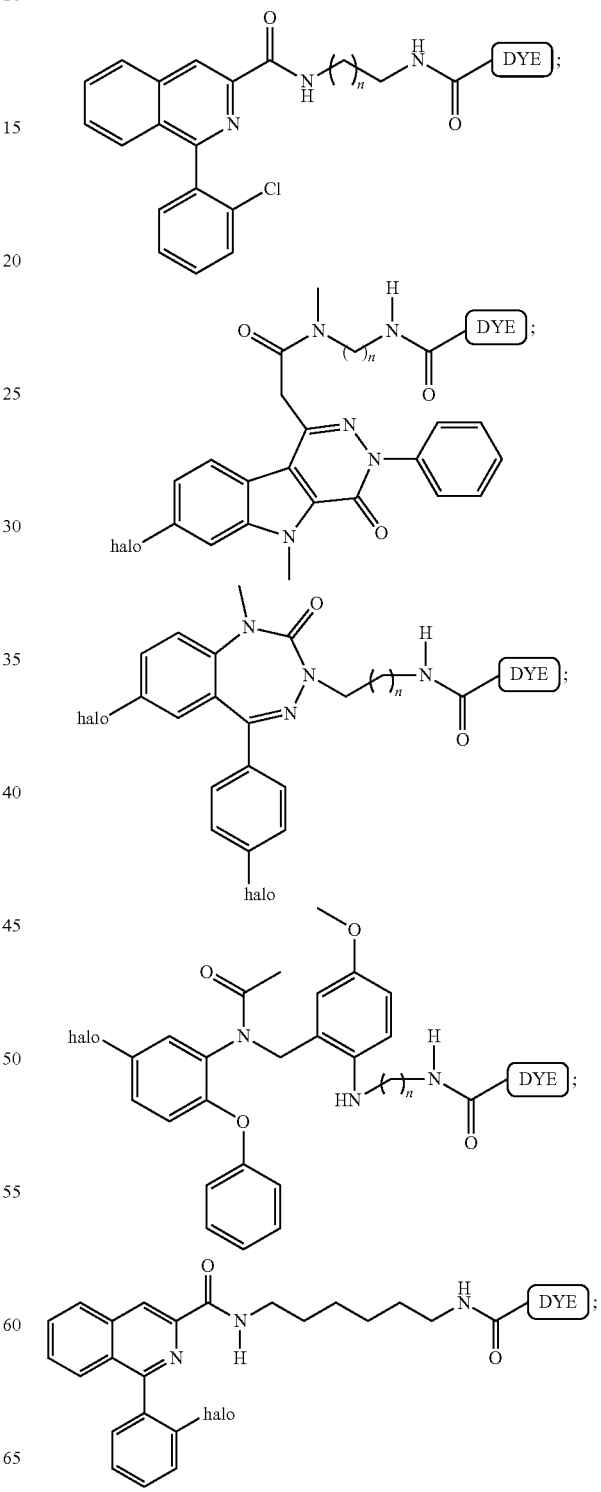

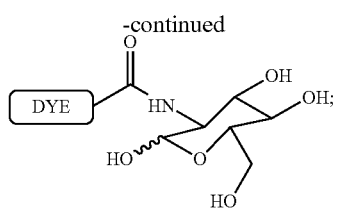

The following compound is an example of one of the coupled compounds described above:

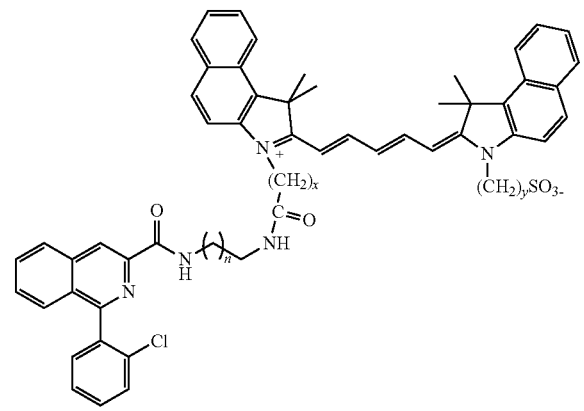

and analogs thereof, wherein n and x are integers from 1 to 10.

As stated above, the compounds of the present invention can be employed as signaling agents in NIR imaging. The resulting signal may be used to image a molecular event. Non-limiting examples of specific molecular events associated with the present invention include at least one of peripheral benzodiazepine expression, cell proliferation, glucose uptake, epidermal growth factor receptor expression, coronary disease.

Thus, the resulting signal may be used to diagnose a disease state such as, for example, cancer, neurodegenerative disease, multiple sclerosis, epilepsy, coronary disease, etc. Specifically, brain cancer and breast cancer are two cancers that may be diagnosed with the compounds and methods of the present invention. Two additional examples are non-Hodgkin's lymphoma and colon cancer.

Another embodiment of the present invention is a method of measuring glucose uptake. This method comprises, comprises administering to a sample a conjugate, the conjugate comprising a conjugable glucosamine compound and a signaling agent; and detecting a signal from said conjugate. As in the other methods, the sample is at least one of cells, tissue, cellular tissue, serum or cell extract. An example of a conjugable glucosamine includes the following compound and conjugable analog thereof:

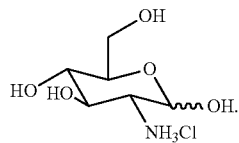

The administration step may be in vivo administration or in vitro administration. The in vivo administration step further comprises at least one time course imaging determination, and in other embodiments, the in vivo administration step further comprises at least one bio distribution determination.

Other embodiments of the present invention include conjugable compounds associated with this glucosamine method, specifically including the following:

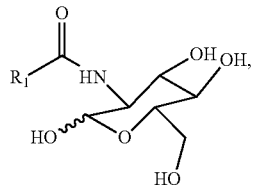

where $R_1$ is a signaling moiety, and

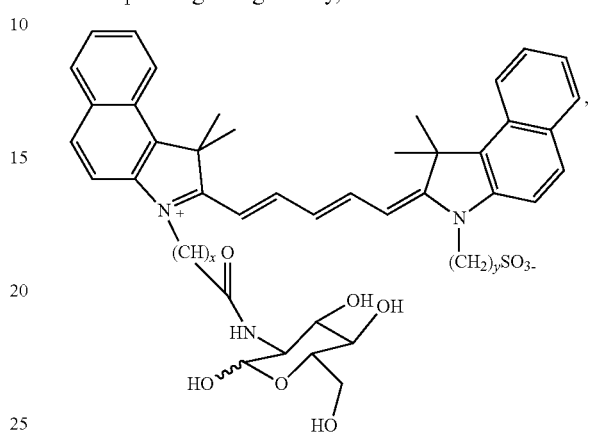

and analogs thereof.

EXAMPLES

The following examples are presented purely for exemplary purposes, and as such the material in this section should be considered as embodiments of the present invention and not to be limiting thereof.

Example 1

This example demonstrates the conjugation of a NIR dye of the present invention and a conjugable analog or conjugable form of PK11195 for deep tissue imaging. In this example, IRDye800CW (LiCOR) is coupled to conjugable PK11195.

Dye800CW-PK11195 (Scheme 1)—To a 10 mL round bottom flask, about 196.5 μL of a 1 mg/ml conjugable PK11195 solution (DMSO) is mixed with about 300 μL of an about 1 mg/mL Dye800CW (DMSO). The reaction proceeds under nitrogen flow for about 1 hour at RT. Reaction progress is monitored via HPLC and ESI MS.

Scheme 1-Conjugation of Succinimidyl Dye to conjugable PK11195

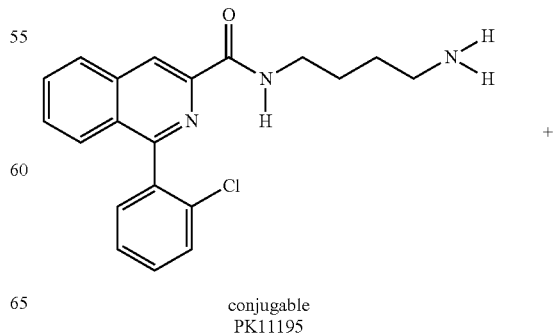

conjugable
PK11195

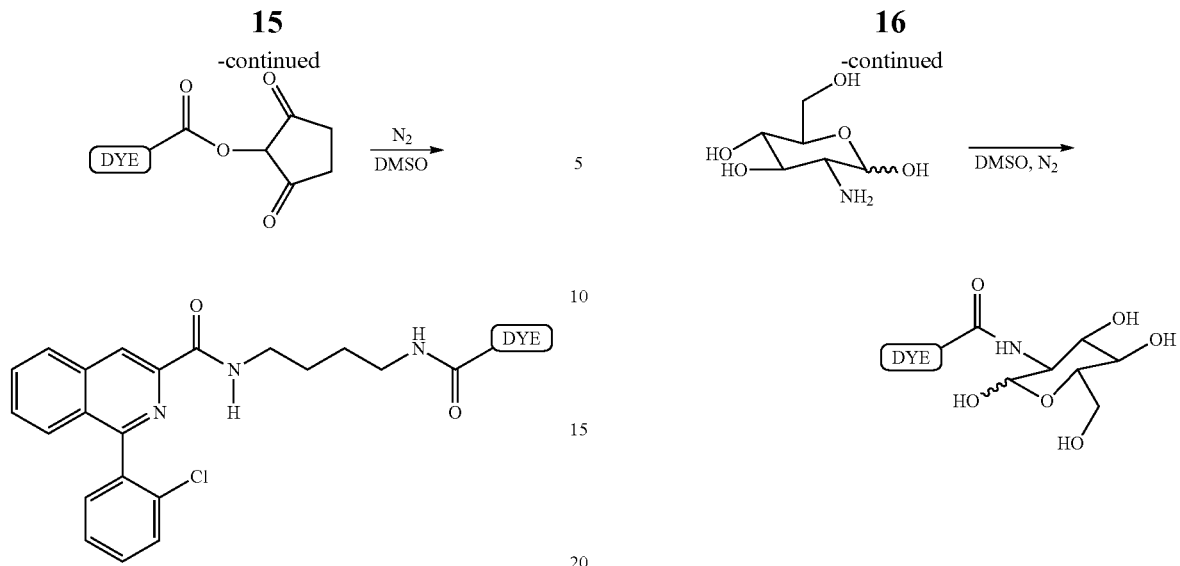

Yield is about 99% and requires no further purification.

Example 2

This example demonstrates an example of the formulation of a NIR-glucosamine conjugate of the present invention.

Dye800CW-Glucosamine (Scheme 2)—To a 10 mL round bottom flask, about 9.3 mg sodium methoxide and about 37 mg D-glucosamine hydrochloride are reacted in about 2 mL DMSO. The solution is stirred under nitrogen for about 3 hours at RT. Next, about 34, of the resulting solution are mixed with about 150 µL of an about 1 mg/mL Dye800CW/DMSO solution in a separate 10 mL flask. The mixture is stirred under nitrogen for another 1.5 hours at RT.

Scheme 2-Conjugation of Succinimidyl Dye to glucosamine

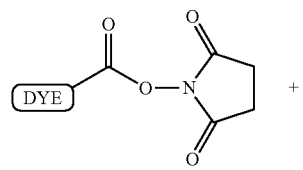

Reaction progress was monitored via HPLC and ESI MS and the reaction yielded 98% pure conjugate.

Example 3

This example demonstrates the use of compounds of the present invention in ESI (Electrospray Ionization) mass spectra.

Initially, about 20 µL of the reaction solution of Example 1 is diluted to about 180 µL using 5 mM ammonium acetate aqueous solution containing about 0.05% acetic acid. The sample is injected the sample immediately into a Mariner ESI mass spectrometer. Some major instrument settings are: spray tip at about 3.4 kv, nozzle potential at about 200 v, quadrupole temperature at about 150° C. and nozzle temperature at about 150° C. Spectra is collected every 100 seconds. In spectrum for Dye800W-glucosamine complex, the expected molecular peak is observed at 1164 Da. In the spectrum for Dye800CW-PK11195 complex, the expected molecular peak is observed at 1365.9 Da.

Example 4

This example shows a synthetic pathway yielding a conjugable Ro5-4864 of the present invention, and conjugation to an imaging agent, such as Lanthanide chelate or NIR-dye.

Scheme 3--Conjugation of Ro5-4864 to Lanthanide Chelator or DYE

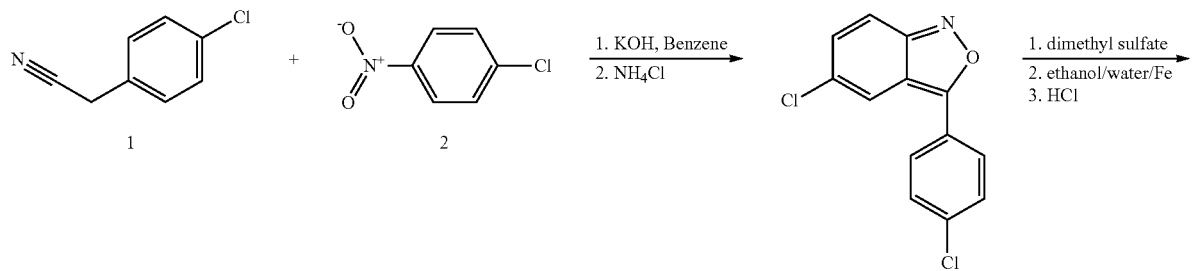

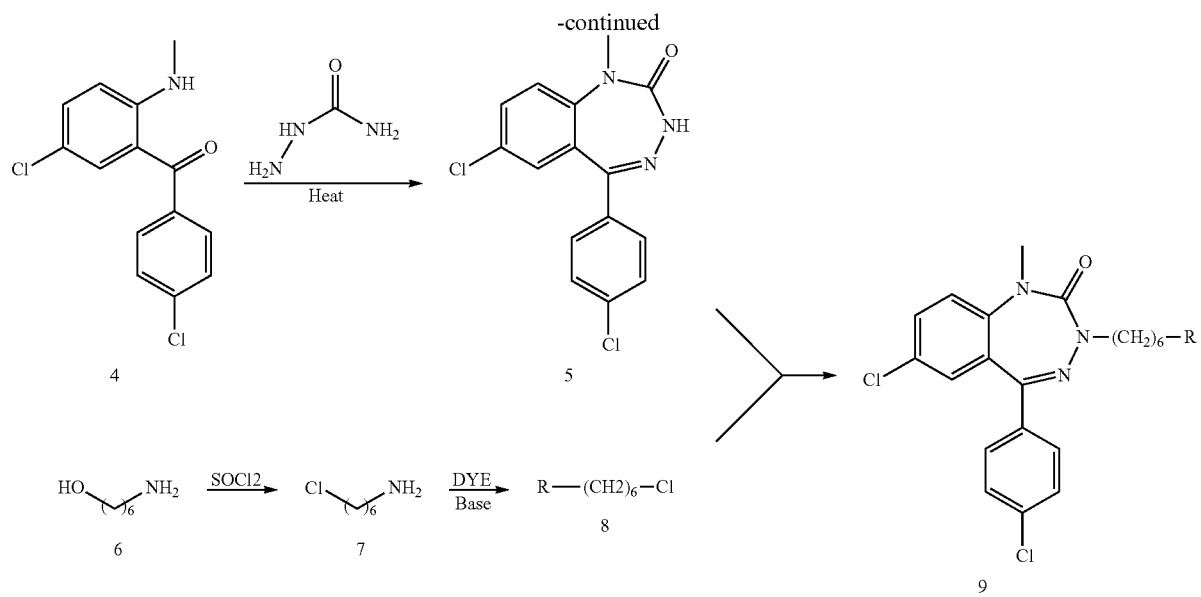

A conjugable form of compounds similar to Ro5-4864 has been previously reported (see U.S. Pat. No. 5,901,381) and a synthetic procedure in Scheme 3 will be used to synthesize a conjugable form of Ro5-4864. A solution of KOH in methanol will be treated with a solution of 4-chlorophenyl-acetonitrile 1 and 4-chloronitro-benzene 2 in benzene. The mixture will be stirred for 3 hours and then poured to ammonium chloride solution. Compound 3 will then precipitate out. Compound 4 will be produced by stirring compound 3 and dimethyl sulfate for 5 hours, followed by being treated with ethanol, water, iron fillings and hydrochloric acid. See Vejdelek Z, Polivka Z, Protiva M. Synthesis of 7-Chloro-5-(4-Chlorophenyl)-1-Methyl-1,3-Dihydro-1,4-Benzodiazepin-2-One. Collection of Czechoslovak Chemical Communications 1985; 50:1064-1069. Compound 4 and semicarbazide, after heated to 210° C., will produce compound 5. Compound 7 will be used as a linker to combine compound 5 and lanthanide chelate/dye800cw. Compound 7 can be synthesized by the reaction between compound 6 and thionyl chloride. Lanthanide chelate (with carboxylic acid group) or dye800cw (a N-hydroxysuccinimide ester) can then react with compound 7 in basic solution to produce a compound in the form of compound 8. The chlorine on the signaling part will react with N—H group in compound 5 to produce the final imaging agent (compound 9). The product can be further chelated by adding lanthanide chloride solution (LnCl$_3$, EuCl$_3$ etc) into product solution with pH 6.5. The synthetic pathway for lanthanide chelate has been reported. See Griffin J M M, Skwierawska A M, Manning H C, Marx J N, Bornhop D J. Simple, high yielding synthesis of trifunctional fluorescent lanthanide chelates. Tetrahedron Letters 2001; 42:3823-3825.

Example 5

This Example shows a scheme for the synthesis of a conjugable form of DAA1106 of the present invention, which cnathen be conjugated to an imaging agent.

Scheme 4-Synthesis of conjugatable DAA1106

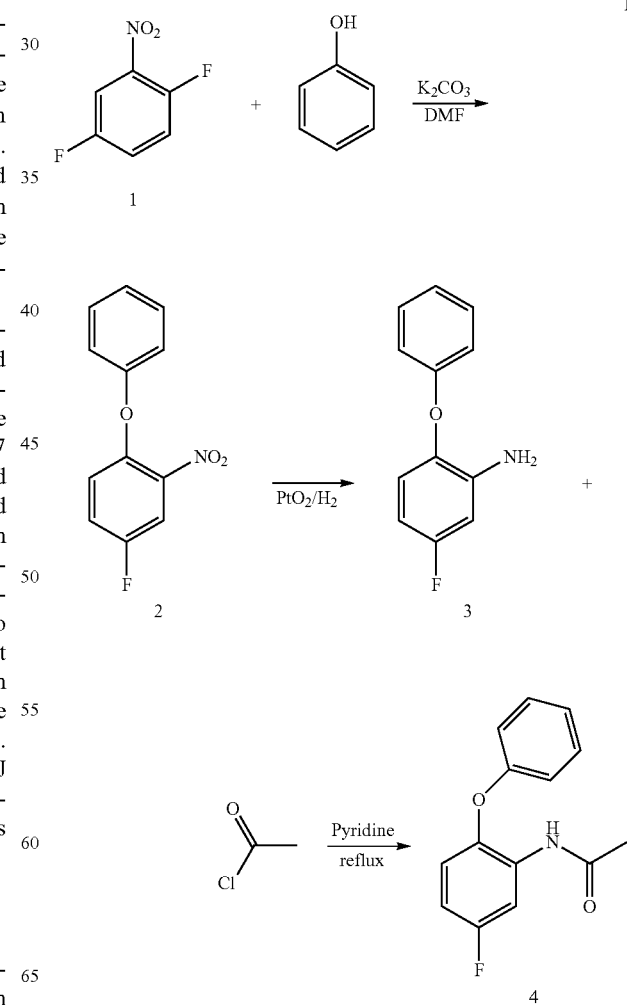

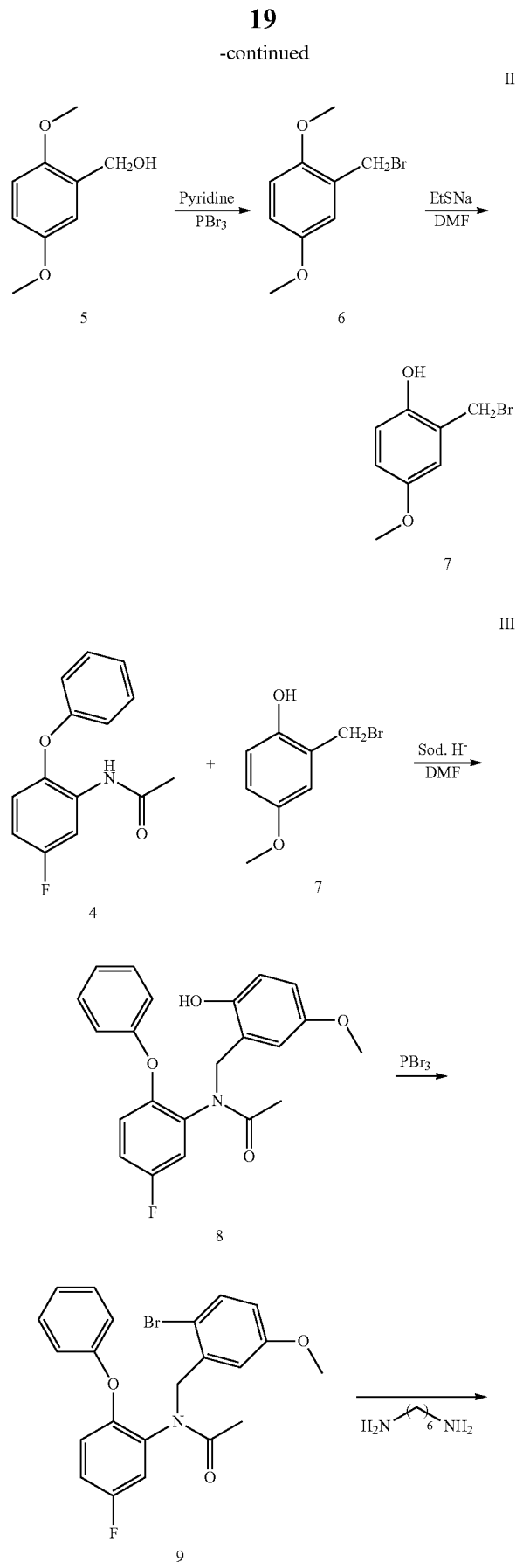

The synthetic pathway for conjugable DAA1106 is shown in Scheme 4. Compound 2 will be obtained by reaction of compound 1 with phenol in DMF. Compound 2 will then be reduced by PtO2 under hydrogen flow in methanol. Compound 3 can react with acetyl chloride in pyridine to produce compound 4 after the reaction refluxes for 2 hours. The hydroxyl group in compound 5 will be substituted by bromide to produce compound 6. One hydroxyl group in compound 6 will be deprotected in DMF by Sodium ethanethiolate to produce compound 7. Compound 4 and 7 will then react in DMF with the presence of sodium hydride. After compound 8 is obtained, the hydroxyl group will be brominated to form compound 9. Conjugable DAA1106 (compound 10) is prepared by treatment of compound 9 with hexane-1,6-diamine. The conjugation position on DAA1106 is determined according to another conjugation that has been done on DAA1106 which did not affect the biological activity of DAA1106. See Zhang M R, Maeda J, Furutsuka K, Yoshida Y, Ogawa M, Suhara T, et al. [F-18]FMDAA1106 and [F-18]FEDAA1106: Two positron-emitter labeled ligands for peripheral benzodiazepine receptor (PBR). Bioorganic & Medicinal Chemistry Letters 2003; 13:201-204. The product should be conjugable to lanthanide chelator in water/DMF/dioxane/TEA mixture. The conjugate will be further chelated by adding Lanthanide chloride solution ($LnCl_3$, $EuCl_3$ etc) into pH 6.5 product solution.

Example 6

This example shows an example of the synthesis, characterization, and preliminary cell study for an embodiment of the present invention, a dye800cw-DAA1106 conjugation, as well as the conjugation of the PBR ligand DAA1106 to a NIR dye, followed by cell uptake.

In this example, dye800CW (5 mg, 4.3 pimp and conjugable DAA1106 (5 mg, 10 μmol) is mixed in DMSO (1 mL) in a 10 mL round bottom flask. The solution is stirred under argon flow for 10 hours. The reaction scheme is shown in Scheme 5, below. Product is purified through neutral alumina column using 0.1 M triethyl ammonium acetate in 80/20 acetonitrile/water solution.

Scheme 5. Reaction scheme for dye800CW-DAA1106

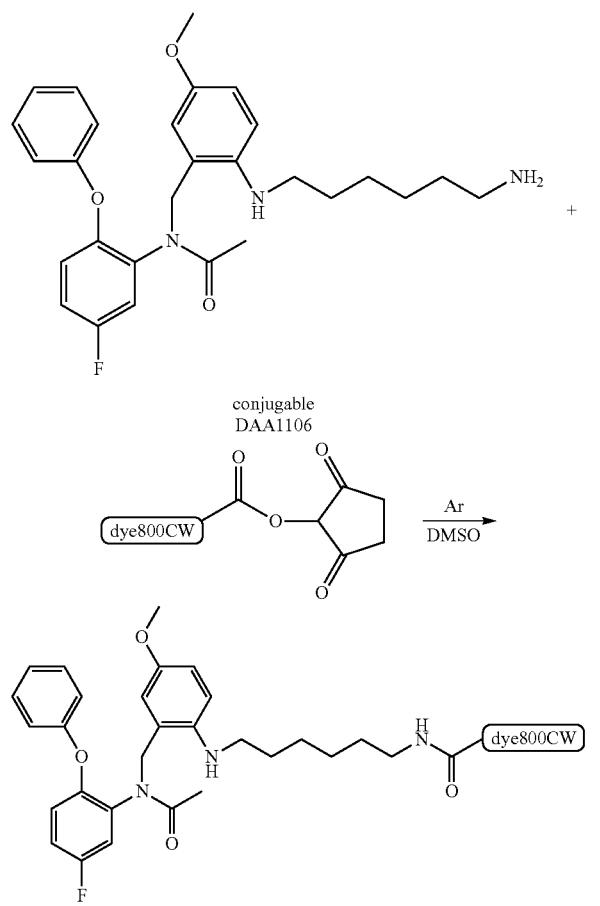

Figure 5:
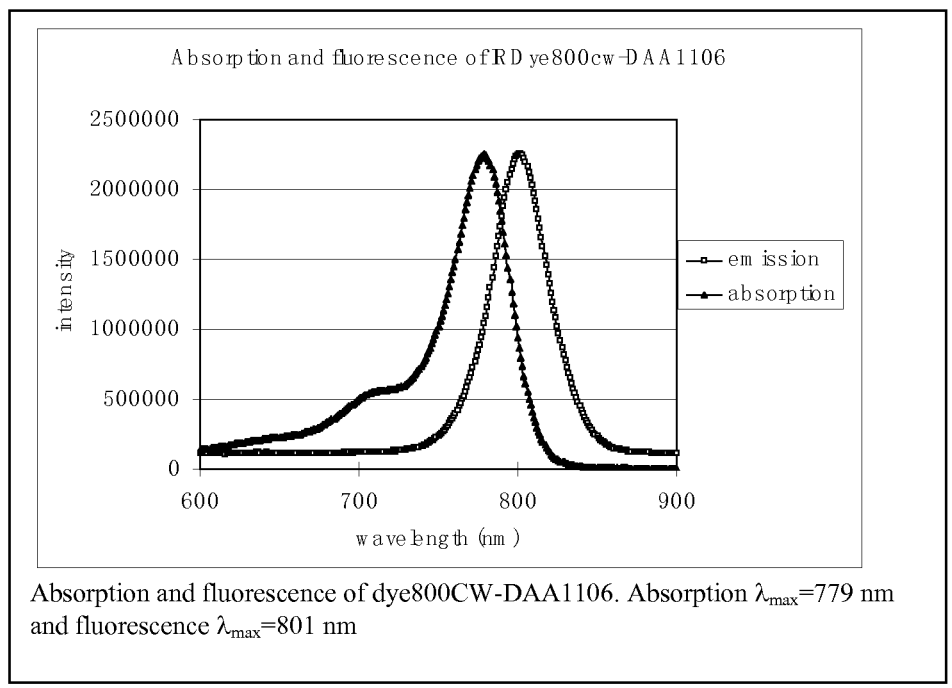
FIG. 5 is a graph that shows absorption and fluorescence of dye 800CW-DAA1006.

Upon preparing dye800CW-DAA1106, absorption and emission spectra (FIG. 5) are obtained at room temperature with a Shimadzu 1700 UV-vis spectrophotometer and ISS PCI spectrofluorometer respectively. The same sample (2 µM) is used for taking both UV and fluorescence spectrum. UV spectrum was scanned from 190 nm to 900 nm with sampling rate of 1 nm. Cuvette path length was 1 cm. Fluorescence sample was excited at 797 nm. Spectrum was collected from 700 nm to 900 nm with scan rate 1 nm/second. Slit width was set to 1.5. Photo multiplier tube (PMT) voltage was at 75 watts. Dye800CW-DAA1106 has maximum absorption at 779 nm and fluorescence at 801 nm in methanol.

Regarding cell uptake, C6 glioma cell lines are a widely used cell line in neurobiological research that has high PBR expression. C6 cells were incubated with 10 µM dye800CW-DAA1106 in culture media for half hour and then rinsed and re-incubated with saline before imaging. FIG. 1 shows white light and fluorescence pictures of dosed and un-dosed cells. Instrument used is Nikon epifluorescence microscope equipped with Ludl Qimaging camera, Nikon S fluor 20×/0.75 objective, mercury lamp and ICG filter set. Picture B shows cell take-up of dye800CW-DAA1106, while un-dosed cell (picture D) does not show any significant fluorescence.

Example 7

This example shows the synthesis, characterization and preliminary cell study of a lissamine-DAA1106 conjugation. An example of a lissamine dye has a molar extinction coefficient of 88,000 cm$^{-1}$M$^{-1}$ and good quantum efficient of about 95%. It absorbs at 568 nm and emits at 583 nm (in methanol) with a decent stokes shift and thus bright fluorescence.

Lissamine rhodamine B sulfonyl chloride (4 mg, 6.9 µmol), conjugable DAA1106 (5 mg, 10 pimp and tri-ethylamine (10 µL) was mixed in dichloromethane (0.8 mL) in a 10 mL round bottom flask. The solution was stirred under argon flow for 3 hours. The reaction scheme is shown in Scheme 6. Product was purified through column chromatography (silica gel) using 19/1 dichloromethane/methanol solution.

Scheme 6. Lissamine-DAA1106 reaction scheme

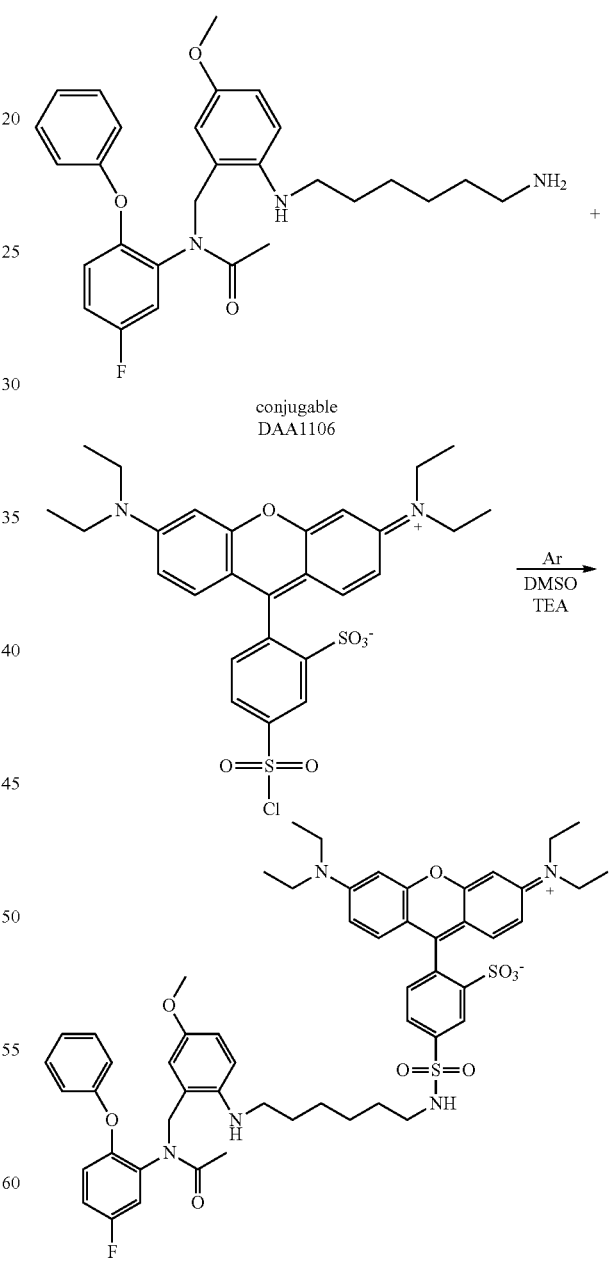

Figure 6:
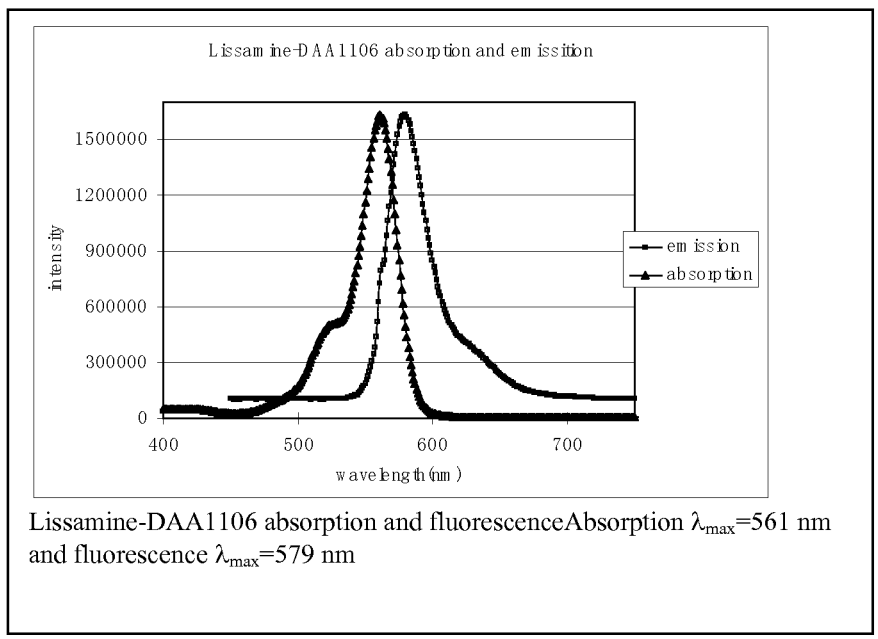
FIG. 6 is a graph that shows lissamine-DAA1006 absorption and fluorescence.

Upon preparing lissamine-DAA1106, absorption and emission spectra (FIG. 6) was obtained with a Shimadzu 1700 UV-vis spectrophotometer and ISS PTI spectrofluorometer at room temperature. The same sample (2 μM) was used for taking both UV and fluorescence spectrum. UV spectrum was scanned from 190 nm to 900 nm with sampling rate of 1 nm. Cuvette path length was 1 cm. Fluorescence sample was excited at 561 nm. Spectrum was collected from 700 nm to 900 nm with scan rate 1 nm/second. Slit width was set to 1.5. Photo multiplier tube (PMT) voltage was at 75 watts. Lissamine-DAA1106 has maximum absorption at 561 nm and fluorescence at 579 nm in methanol.

Figure 2:
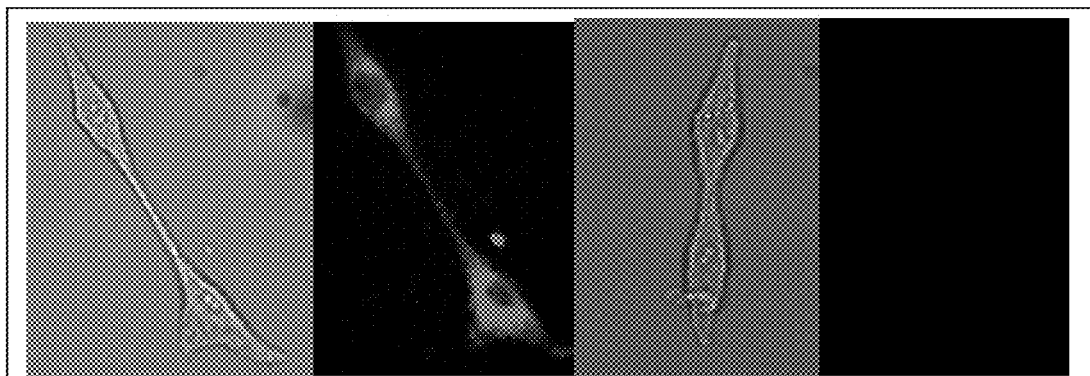
FIG. 2 is a color photograph that shows white light and fluorescence pictures of dosed cells and un-dosed cells in accordance with the present invention, and is further discussed in Example 7, below. Picture A is a white light picture of dosed cells, Picture B is a fluorescence picture of dosed cells, Picture C is a white light picture of un-dosed cells, and Picture D is a fluorescence picture of un-dosed cells.

C6 cells were incubated with 10 μM lissamine-DAA1106 in culture media for half hour and then rinsed and re-incubated with saline before imaging. FIG. 2 shows white light and fluorescence pictures of dosed and un-dosed cells. Instrument used was Nikon epifluorescence microscope equipped with Ludl Qimaging camera, Nikon S fluor 20×/0.75 objective, mercury lamp and Texas red filter set. Picture B shows cell take-up of lissamine-DAA1106 at perinuclear location. This observation was expected since PBR is a mitochondrial protein. Un-dosed cells (picture D) exhibited no fluorescence.

Example 8

This example shows an example of a synthetic pathway yielding a conjugable form of a SSR180575 compound of the present invention.

Starting from m-chloroaniline, which was diazotised and coupled with ethyl α-methylacetoacetate, the azo-ester was converted into ethyl pyruvate m-chlorophenylhydrazone 1 (the Japp-Klingeman reaction). Polyphosphoric acid facilitated the conversion to molecule 2. Next, N-methylation with dimethylcarbonate in presence $K_2CO_3$ yielded the ester 3 and was treated with hydrazine and converted into hydrazide 4. The ring was closed in the presence of $POCl_3$ and compound 5 was obtained. N-phenylation with using PhI and CuI (as catalyst) provide compound 6. Mild hydrolysis with dilute KOH in EtOH yield acid 7. To conjugated mono-N—BOC protected N-methyl-1,6-hexanediamine to 7 used BOP. Removal of protecting group with TFA in $CH_2Cl_2$ is yields 8.

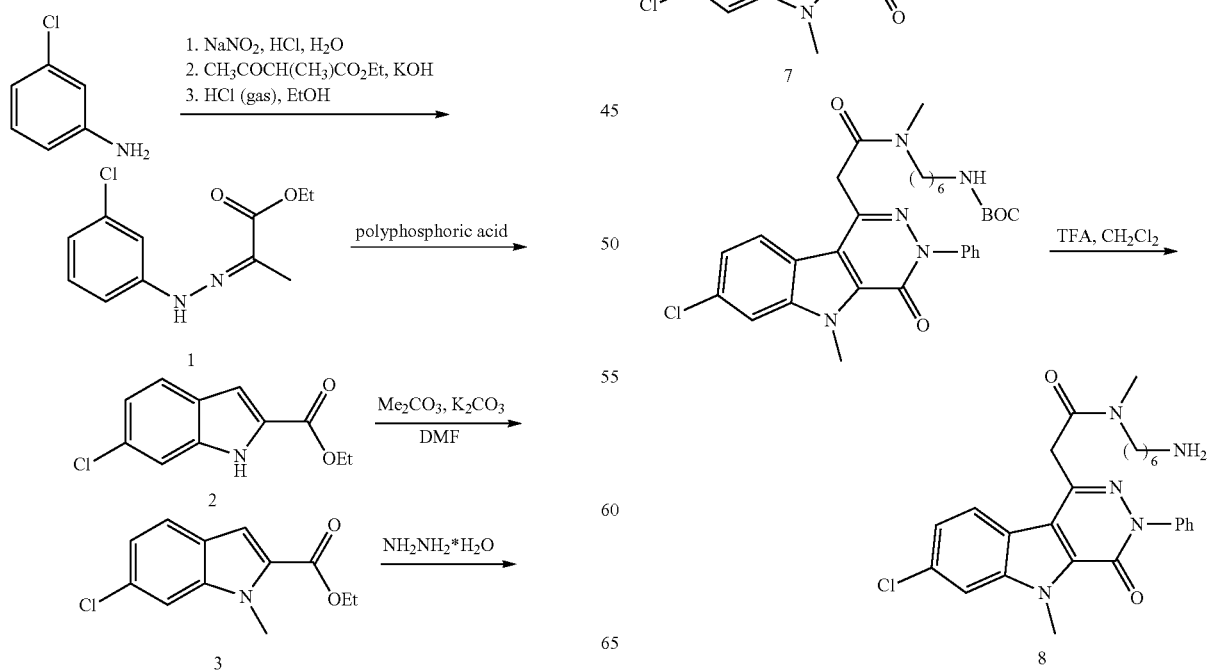

Example 9

Figure 3:
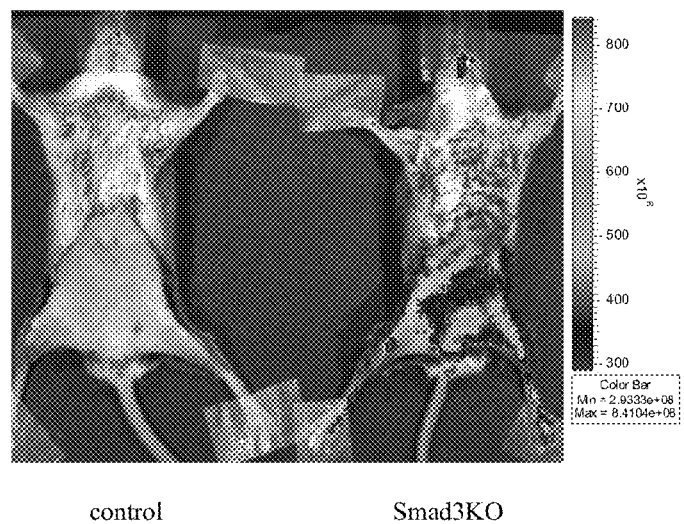
FIG. 3 is a color photograph that shows in vivo cancer imaging of a small laboratory animal.
Figure 4:
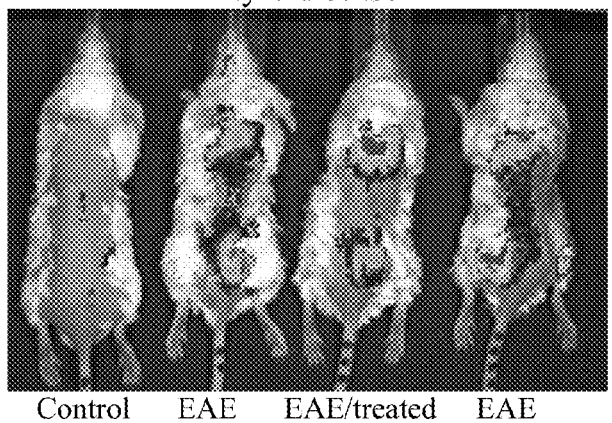
FIG. 4 is a color photograph that shows in vivo neurodegenerative imaging of a small laboratory animal.
Figure 4:
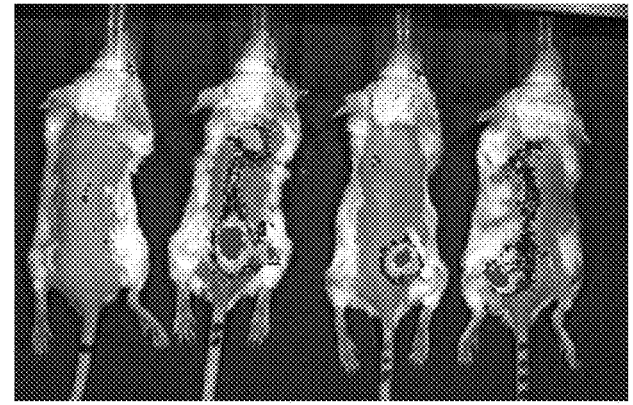

Example 9 demonstrates specific, in vivo tumor labeling using a method of the present invention. A NIR-PK 11195 deep tissue imaging agent was made as shown in Example 1. Tumor bearing Smad3 gene knockout mice and control animals were injected with 10 nmoles of the imaging agent and imaged about 14 hours following injection. Specific labeling was observed in the abdominal region of tumor animals and clearance in the control animals. This selective uptake is shown in FIG. 3. A post-imaging autopsy confirmed localization of the imaging agent in the SMAD3 animal.

Example 10

This Example shows NIR-PK 11195 imaging in connection with neurodegenerative processes in experimental autoimmune encephalomyelitis (EAE), the animal model of multiple sclerosis. Additionally, this Example shows the use of the present invention to monitor the progression of a disease state. A conjugated imaging agent NIR-PK 11195 was made in accordance with Example 1. An EAE induced and control animals were injected with NIR-PK 11195 and imaged. EAE animals demonstrate strong fluorescence along the spinal column indicating activated T cell and macrophage response which signal the onset of the demylenation processes characteristic to EAE. The EAE/treated mouse was treated with a curcumin composition.

FIG. 3 shows images associated with this example that confirm insignificant uptake of the imaging agent in the control, but indicate full onset of a disease state in the EAE mice. Subsequent imaging shows the progression of the disease after a disease state treatment is administered.

References

Throughout this application, various publications are referenced. All such publications, specifically including the publications listed below, are incorporated herein by reference in their entirety.

1. Manning H C, Goebel, T. S. Thompson, R. C., and Bornhop, D. J. A PBR Targeted Molecular Imaging Agent for Cellular-Scale Bi-modal Imaging. Bioconjugate Chemistry 2003; *Bioconjugate Chem* 2004, 15, 1488-1495.
2. Broaddus W C, Bennett J P, Jr., Department of Neurosurgery UoVHSCC. Peripheral-type benzodiazepine receptors in human glioblastomas: pharmacologic characterization and photoaffinity labeling of ligand recognition site. Brain research. 1990; 518(1-2):199-208.
3. Zhang M R, Maeda J, Furutsuka K, Yoshida Y, Ogawa M, Suhara T, et al. [F-18]FMDAA1106 and [F-18]FEDAA1106: Two positron-emitter labeled ligands for peripheral benzodiazepine receptor (PBR). Bioorganic & Medicinal Chemistry Letters 2003; 13:201-204.
4. Kozikowski A P, Kotoula M, Ma D, Boujrad N, Tueckmantel W, Papadopoulos V. Synthesis and Biology of a 7-Nitro-2,1,3-benzoxadiazol-4-yl Derivative of 2-Phenylindole-3-acetamide: A Fluorescent Probe for the Peripheral-Type Benzodiazepine Receptor. Journal of Medicinal Chemistry 1997; 40:2435-2439.
5. Starosta-Rubinstein S, Ciliax B, Penney J, McKeever P, Young A. Imaging of a glioma using peripheral benzodiazepine receptor ligands. proceedings of the national academy of sciences of the United States of America 1987; 84:891-5.
6. Black K L, Ikezaki K, Toga A W. Imaging of Brain-Tumors Using Peripheral Benzodiazepine Receptor Ligands. Journal of Neurosurgery 1989; 71:113-118.
7. Sutter A P, Maaser K, Hèopfner M, Barthel B, Grabowski P, Faiss S, et al. Specific ligands of the peripheral benzodiazepine receptor induce apoptosis and cell cycle arrest in human esophageal cancer cells. International journal of cancer. Journal international du cancer. 2002; 102(4):318-27.
8. Jakubikova J, Duraj J, Hunakova L, Chorvath B, Sedlak J. PK11195, an isoquinoline carboxamide ligand of the mitochondrial benzodiazepine receptor, increased drug uptake and facilitated drug-induced apoptosis in human multidrug-resistant leukemia cells in vitro. Neoplasma 2002; 49:231-236.
9. Okaro A C, Fennell D A, Corbo M, Davidson B R, Cotter F E. Pk11195, a mitochondrial benzodiazepine receptor antagonist, reduces apoptosis threshold in Bcl-X-L and Mcl-1 expressing human cholangiocarcinoma cells. Gut 2002; 51:556-561.
10. Okaro M C, Fennel D A, Corbo M, Cotter F E, Davidson B R, Winslet M C. In vivo reversal of apoptosis resistance by the mitochondrial benzodiazepine receptor antagonist, PK11195 in cholangiocarcinoma cells. Gut 2000; 46:A47-A47.
11. Okaro M C, Fennell D A, Cotter F E, Davidson B R. Pk11195, a mitochondrial benzodiazepine receptor antagonist radiosensitizes bcl-x(L) and mcl-1 expressing cholangiocarcinoma to apoptosis. British Journal of Cancer 2000; 83:22-22.
12. Maaser K, Hèopfner M, Jansen A, Weisinger G, Gavish M, Kozikowski A P, et al. Specific ligands of the peripheral benzodiazepine receptor induce apoptosis and cell cycle arrest in human colorectal cancer cells. British journal of cancer. 2001; 85(11):1771-80.
13. Fennell D A, Corbo M, Pallaska A, Cotter F E. Bcl-2 resistant mitochondrial toxicity mediated by the isoquinoline carboxamide PK11195 involves de novo generation of reactive oxygen species. British Journal of Cancer 2001; 84:1397-1404.
14. Ntziachristos V, Chance B. Probing physiology and molecular function using optical imaging: applications to breast cancer. Breast Cancer Research 2001; 3:41-46.
15. Licha K, Riefke B, Ntziachristos V, Becker A, Chance B, Semmler W. Hydrophilic cyanine dyes as contrast agents for near-infrared tumor imaging: Synthesis, photophysical properties and spectroscopic in vivo characterization. Photochemistry and Photobiology 2000; 72:392-398.
16. Hawrysz D J, Sevick-Muraca E M. Developments toward diagnostic breast cancer imaging using near-infrared optical measurements and fluorescent contrast agents. Neoplasia 2000; 2:388-417.
17. Weissleder R, Mahmood U. Molecular imaging. Radiology 2001; 219:316-333.
18. Gaietta G, Deerinck T J, Adams S R, Bouwer J, Tour O, Laird D W, et al. Multicolor and electron microscopic imaging of connexin trafficking. Science 2002; 296:503-507.
19. Louie A Y, Huber M M, Ahrens E T, Rothbacher U, Moats R, Jacobs R E, et al. In vivo visualization of gene expression using magnetic resonance imaging. Nature Biotechnology 2000; 18:321-325.
20. Wolfe H R, Mendizabal M, Lleong E, Cuthbertson A, Desai V, Pullan S, et al. In vivo imaging of human colon cancer xenografts in immunodeficient mice using a guanylyl cyclase C-specific ligand. Journal of Nuclear Medicine 2002; 43:392-399.
21. Lemieux G A, Yarema K J, Jacobs C L, Bertozzi C R. Exploiting differences in sialoside expression for selective targeting of MRI contrast reagents. Journal of the American Chemical Society 1999; 121:4278-4279.
22. Casellas P, Galiegue S, Basile A S. Peripheral benzodiazepine receptors and mitochondrial function. Neurochemistry International 2002; 40:475-486.
23. Hardwick M, Fertikh D, Culty M, Li H, Vidic B, Papadopoulos V. Peripheral-type benzodiazepine receptor (PBR) in human breast cancer: Correlation of breast cancer cell aggressive phenotype with PBR expression, nuclear localization, and PBR-mediated cell proliferation and nuclear transport of cholesterol. Cancer Research 1999; 59:831-842.
24. Papadopoulos V. Peripheral-Type Benzodiazepine Diazepam Binding Inhibitor Receptor—Biological Role in Steroidogenic Cell-Function. Endocrine Reviews 1993; 14:222-240.
25. Alho H, Varga V, Krueger K E. Expression of Mitochondrial Benzodiazepine Receptor and Its Putative Endogenous Ligand in Cultured Primary Astrocytes and C-6 Cells—Relation to Cell-Growth. Cell Growth & Differentiation 1994; 5:1005-1014.
26. Diorio D, Weiner S A, Butterworth R F, Meaney M J, Suranyicadotte B E. Peripheral Benzodiazepine Binding-Sites in Alzheimers-Disease Frontal and Temporal Cortex. Neurobiology of Aging 1991; 12:255-258.
27. Messmer K, Reynolds G P. Increased peripheral benzodiazepine binding sites in the brain of patients with Huntington's disease. Neuroscience Letters 1998; 241: 53-56.
28. Vowinckel E, Reutens D, Becher B, Verge G, Evans A, Owens T, et al. PK11195 binding to the peripheral benzodiazepine receptor as a marker of microglia activation in multiple sclerosis and experimental autoimmune encephalomyelitis. Journal of Neuroscience Research 1997; 50:345-353.
29. Benavides J, Cornu P, Dennis T, Dubois A, Hauw J J, Mackenzie E T, et al. Imaging of Human-Brain Lesions with an Omega-3 Site Radioligand. Annals of Neurology 1988; 24:708-712.
30. Cornu P, Benavides J, Scatton B, Hauw J J, Philipp on J. Increase in Omega-3 (Peripheral-Type Benzodiazepine) Binding-Site Densities in Different Types of Human Brain-Tumors—a Quantitative Autoradiography Study. Acta Neurochirurgica 1992; 119:146-152.
31. Shavaleev N M, Pope S J A, Bell Z R, Faulkner S, Ward M D. Visible-light sensitisation of near-infrared luminescence from Yb(III), Nd(III) and Er(III) complexes of 3,6-bis(2-pyridyl)tetrazine. Dalton Transactions 2003: 808-814.
32. Werts M H V, Verhoeven J W, Hofstraat J W. Efficient visible light sensitisation of water-soluble near-infrared luminescent lanthanide complexes. Journal of the Chemical Society-Perkin Transactions 2 2000:433-439.
33. Werts M H V, Hofstraat J W, Geurts F A J, Verhoeven J W. Fluorescein and eosin as sensitizing chromophores in near-infrared luminescent ytterbium(III), neodymium (III) and erbium(III) chelates. Chemical Physics Letters 1997; 276:196-201.
34. Faulkner S, Pope S J A. Lanthanide-sensitized lanthanide luminescence: Terbium-sensitized ytterbium luminescence in a trinuclear complex. Journal of the American Chemical Society 2003; 125:10526-10527.
35. Bromiley A, Welch A, Chilcott F, Waikar S, McCallum S, Dodd M, et al. Attenuation correction in PET using consistency conditions and a three-dimensional template. Ieee Transactions on Nuclear Science 2001; 48:1371-1377.
36. Couper G W, McAteer D, Wallis R, Welch A, Norton M, Park K G M. Quantification of FDG-PET scans in patients with oesophageal and gastric cancer. A study of 40 patients. British Journal of Surgery 2002; 89:64-64.
37. Couper G W, Wallis F, Welch A, Sharp P F, Park K G M, Cassidy J. The role of FDG-PET in the early detection of response of colorectal liver metastases to chemotherapy. Gut 2002; 50:A107-A107.
38. Dehdashti F, Flanagan F L, Mortimer J E, Katzenellenbogen J A, Welch M J, Siegel B A. Positron emission tomographic assessment of "metabolic flare" to predict response of metastatic breast cancer to antiestrogen therapy. European Journal of Nuclear Medicine 1999; 26:51-56.
39. Oyama N, Kim J, Jones L A, Mercer N M, Engelbach J A, Sharp T L, et al. MicroPET assessment of androgenic control of glucose and acetate uptake in the rat prostate and a prostate cancer tumor model. Nuclear Medicine and Biology 2002; 29:783-790.
40. Oyama N, Miller T R, Dehdashti F, Siegel B A, Fischer K C, Michalski J M, et al. C-11-acetate PET imaging of prostate cancer: Detection of recurrent disease at PSA relapse. Journal of Nuclear Medicine 2003; 44:549-555.
41. Smith I C, Welch A, Chilcott F, Soloviev D, Waikar S, Hutcheon A W, et al. F-18-FDG PET may predict the pathological response of breast cancer to primary chemotherapy. Journal of Nuclear Medicine 1999; 40:137p-137p.
42. Smith I C, Welch A E, Hutcheon A W, Miller I D, Payne S, Chilcott F, et al. Positron emission tomography using [F-18]-fluorodeoxy-D-glucose to predict the pathologic response of breast cancer to primary chemotherapy. Journal of Clinical Oncology 2000; 18:1676-1688.
43. Manning H C, Goebel T, Marx J N, Bornhop D J. Facile, efficient conjugation of a trifunctional lanthanide chelate to a peripheral benzodiazepine receptor ligand. Organic Letters 2002; 4:1075-1078.
44. Zhang M, Zhang Z H, Blessington D, Li H, Busch T M, Madrak V, et al. Pyropheophorbide 2-deoxyglucosamide: A new photosensitizer targeting glucose transporters. Bioconjugate Chemistry 2003; 14:709-714.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

We claim:

1. A method of imaging a molecular event in a sample, comprising:
   (a) forming a probe comprising the following formula:

[chemical structure]

wherein n is 0-10, and a near-infrared signaling agent binded thereto;
   (b) administering to said sample a probe having an affinity for a target; and
   (c) detecting a signal from said probe.

2. The method of claim 1, wherein said sample is at least one of cells, tissue, cellular tissue, serum, cell extract, bodily fluids.

3. The method of claim 2, wherein the bodily fluids are breast milk, sputum, vaginal fluids, urine.

4. The method of claim 1, wherein the administering step is in vivo or in vitro.

5. The method of claim 1, wherein said molecular event is at least one of peripheral benzodiazepine receptor expression, cell proliferation, glucose uptake, epidermal growth factor receptor expression, microglial activation, apoptosis, matrix metalloproteinase activation.

6. The method of claim 1, further comprising the step of: analyzing said signal to diagnose a disease state.

7. The method of claim 6, wherein the disease state is cancer, neurodegenerative disease, cancer, multiple sclerosis, epilepsy.

8. The method of claim 6, wherein the disease state is brain cancer or breast cancer.

9. The method of claim 1, wherein the signaling agent is a cyanine dye.

10. The method of claim 1, wherein the signaling agent is a compound of the following formula, or a conjugable form thereof:

[chemical structure]

wherein R is —OH, —CO$_2$H, —NH$_2$, —NCS and each of x and y, independently, is an integer selected from 1 to about 10.

11. The method of claim 1, wherein the probe is a compound of the formula:

[chemical structure]

and analogs thereof, wherein n and x are integers from 1 to 10.

12. A method for delivering an agent to a sample of cells, comprising:
    (a) forming a conjugate comprising the following formula:

[chemical structure]

wherein n is 0-10, and an infrared signaling agent binded thereto; and
    (b) introducing the conjugate to the sample of cells.

13. A compound of the formula:

[chemical structure]

or an analog thereof, wherein R$_1$ is an infrared signaling agent; "halo" is fluorine, chlorine, bromine, iodine; and n is 0-10.

14. The compound of claim 13, wherein the infrared signaling agent is a fluorophore dye.

15. A compound of the formula:

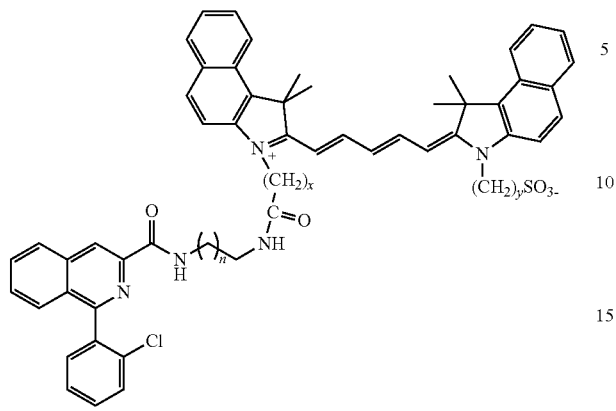

and an analog thereof, wherein n and x are integers from 1 to 10.

16. A compound of claim 13, wherein the infrared signaling agent is a fluorescent dye.

17. The compound of claim 16, wherein the dye is a lissamine dye.

18. The compound of claim 17, wherein the lissamine dye is a lissamine rhodamine B sulfonyl chloride dye.

19. The compound of claim 13, wherein the infrared signaling agent is a cyanine dye.

* * * * *